United States Patent [19]

Van Driel

[11] Patent Number: 5,755,705
[45] Date of Patent: May 26, 1998

[54] HALF-DEFINED INLET CONNECTOR FOR HARDSHELL RESERVOIRS

[75] Inventor: Michael R. Van Driel, Fountain Valley, Calif.

[73] Assignee: Medtronic, Inc., Minneapolis, Minn.

[21] Appl. No.: 728,872

[22] Filed: Oct. 10, 1996

[51] Int. Cl.⁶ ............................................. A61B 17/43
[52] U.S. Cl. ...................... 604/283; 285/239; 285/905
[58] Field of Search ................... 604/283, 93, 905, 604/175, 322, 326; 285/239, 148.27

[56] References Cited

U.S. PATENT DOCUMENTS

| | | | |
|---|---|---|---|
| 3,802,433 | 4/1974 | Raven | 128/214.4 |
| 4,526,572 | 7/1985 | Donnan et al. | 604/29 |
| 4,597,594 | 7/1986 | Kacalieff et al. | 285/239 |
| 4,619,640 | 10/1986 | Potolsky et al. | 604/7 |

OTHER PUBLICATIONS

Avecor Affinity CVR Instructions for use (publication date unknown but believed to be less than one year prior to filing date of present case.).

Primary Examiner—Michael Powell Buiz
Assistant Examiner—Deborah Blyveis
Attorney, Agent, or Firm—Harry G. Weissenberger

[57] ABSTRACT

In a connector for a hardshell venous reservoir, improved positioning and better line holding ability is provided by forming a line-retaining barb on only the upper half of the connector. A dual-size or combo connector using this principle is also disclosed.

4 Claims, 3 Drawing Sheets

HALF-DEFINED INLET CONNECTOR FOR HARDSHELL RESERVOIRS

FIELD OF THE INVENTION

This invention relates to inlet connectors for a hardshell reservoir, and more particularly to a connector in which the line attachment barb is defined around only one half of the connector's circumference.

BACKGROUND OF THE INVENTION

Hardshell reservoirs, such as are used, for example, as combined venous reservoirs and cardiotomy filter/defoamers in cardiac surgery, conventionally have a rigid cover on which a number of line connectors are mounted. To avoid kinking of the lines, which come from locations sideways of the reservoir, the connectors must extend from a manifold in a generally horizontal direction, i.e. more or less parallel to the cover.

To avoid failure-risking joints and assembly labor, connectors such as cardiotomy inlet connectors are conventionally formed together with the cover, or with a manifold connected to the cover, in a single molding operation. It is also desirable to have the connectors lie as closely to the cover as possible so as to avoid the imposition of bending stresses on the connector necks during attachment of the lines.

This proximity requirement, however, poses a problem in the molding operation. Typically, the connector is formed between an upper die and a lower die which are mated during the injection of plastic into the mold. When the plastic has set, the dies are separated and removed. In order to clear the line attachment barb which is formed on the connector, the dies must be pulled away in a direction perpendicular to the axis of the connector. For the upper die, this is no problem, as it is free to move upwardly. The lower die, however, cannot move downwardly if the connector is very close to the cover. Rather, it would have to slide off the connector in an axial direction, but it cannot do this if an annular line-retaining barb is formed on the connector. This circumstance has in the past required a substantial minimum spacing between the connectors and the cover.

SUMMARY OF THE INVENTION

The present invention allows the use of an axially sliding die under the cardiotomy connectors, and therefore a very small spacing between the connectors and the cover, by forming the line-attaching barb only on the upper side of the connectors. This half-defined barb construction has substantial advantages not only in the manufacturing process, but also in use, as it results in a tighter, less easily disengageable connection.

In another aspect of the invention, the half-defined barb is used in connection with a dual-size cardiotomy connector which makes the hardshell reservoir adaptable to the varying requirements of different countries without giving up the proximity advantage.

DESCRIPTION OF THE PREFERRED EMBODIMENT

Figure 1A:
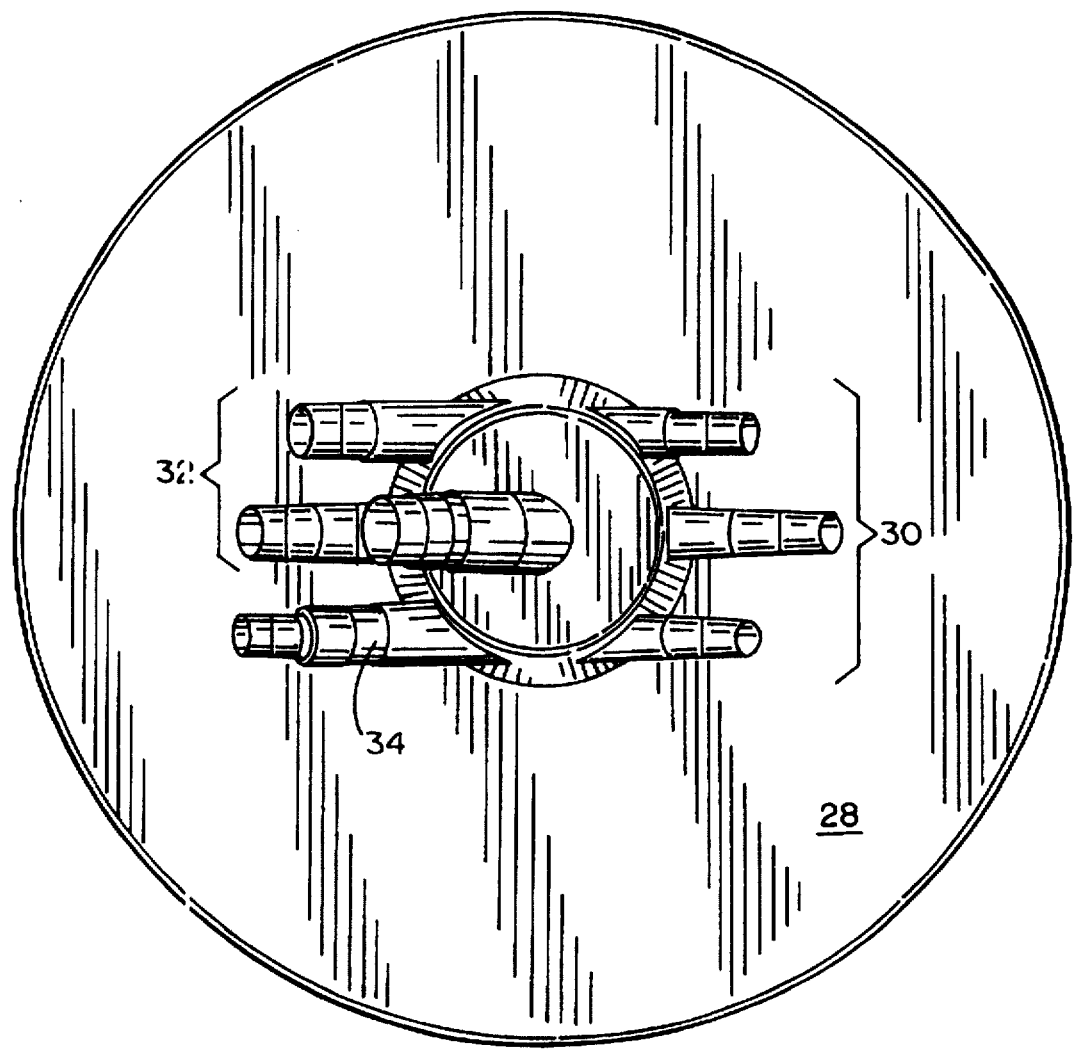
FIG. 1a is a plan view and FIG. 1b is a vertical cross section, of a venous reservoir using the invention.

FIG. 1 illustrates the environment in which the invention is useful. A hardshell reservoir 10 contains a cardiotomy chamber 12 defined by a cylindrical filter/defoamer 14 through which cardiotomy blood entering through the cardiotomy connectors 16 exits into the reservoir body 18. A flow tube 20 conveys venous blood from the venous inlet connector 22 to the venous chamber 24, from which it exits into the reservoir body 18 through a defoamer 26.

Figure 1B:
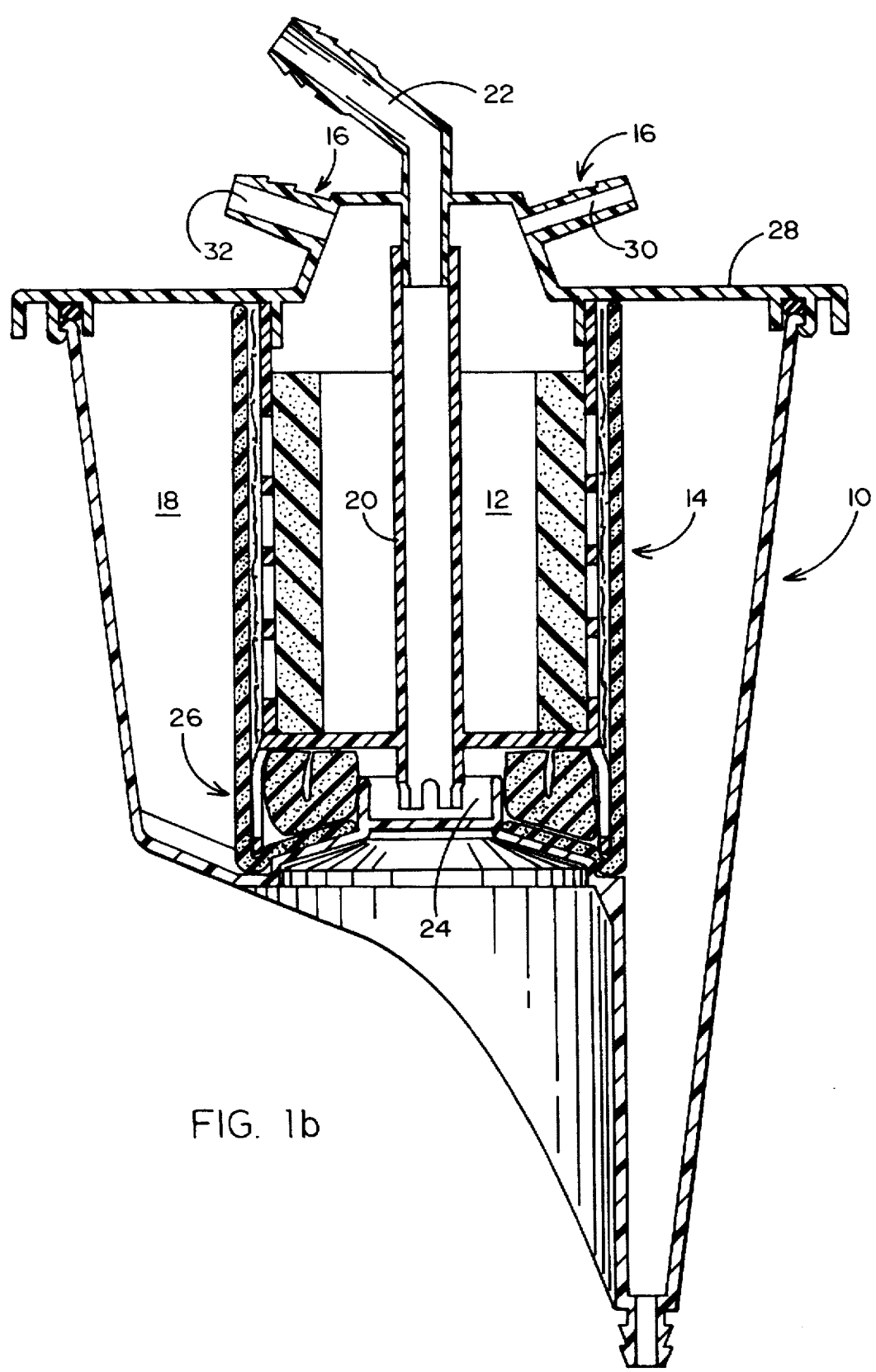

FIG. 1b shows a preferred arrangement of the cardiotomy inlet connectors for Western world markets. In the United States, perfusionists typically prefer quarter-inch (6.35 mm) diameter connectors, while European perfusionists tend to favor ⅜" (9.5 mm) connectors. Because the use of 2–4 cardiotomy inlets is common in the United States, and 2–3 inlets is common in Europe, the central cover 28 preferably carries three quarter-inch connectors 30 on one side, and two 9.5 mm connectors 32 and one dual-size connector 34 on the other. The dual-size or combo connector 34 can take either a quarter-inch line or a 9.5 mm line, and is discussed in more detail below.

Figure 2:
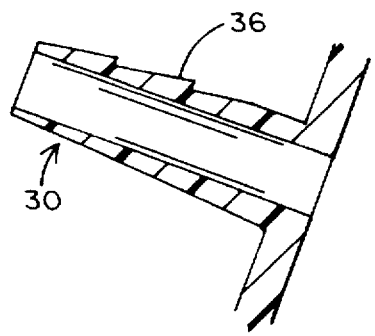
FIG. 2 is a vertical axial section of a cardiotomy connector according to the invention.
Figure 3A:
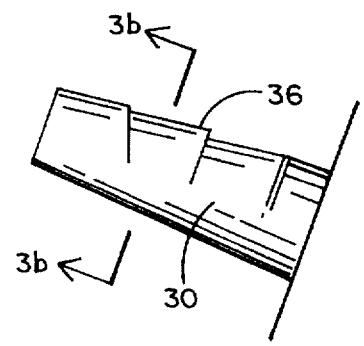
FIG. 3a is a side elevation, and FIG. 3b an axial front elevation, of the connector of FIG. 2.
Figure 3B:
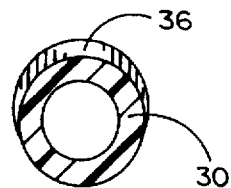

FIGS. 2 and 3 show the inventive half-defined barb construction on a quarter-inch connector 30. The connector 30 may be cylindrical, or it may have a slightly conical shape, but in either event it is characterized that the line retention barbs 36 are formed only on the upper half of the connector 30, with the lower half of the connector 30 being smooth throughout its relevant length.

Figure 4:
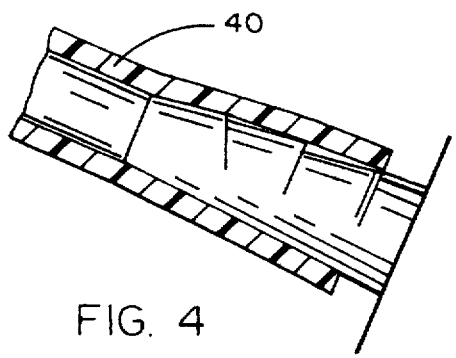
FIG. 4 is a vertical axial section of the connector of FIG. 2 with a line attached.

As best shown in FIG. 4, the half-defined barb construction of FIGS. 2 and 3 is advantageous not only in manufacture, but also in use. When the line 40 is pushed onto the connector 30, the entire lower half of the line 40 lies snugly against the connector 30 and forms a long uninterrupted seal with the connector 30. The resulting large contact area also opposes any disengagement with considerable friction.

At the same time, the barbs 36 on the upper half of the connector 34 bite into the line 40 in the conventional manner to prevent disengagement of the line 40 with a quick jerky motion.

Figure 5:
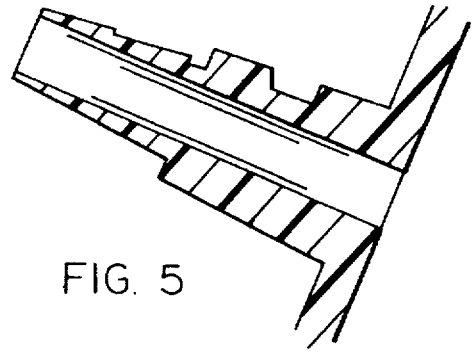
FIG. 5 is a vertical axial section of a dual-size connector according to the invention.
Figure 6A:
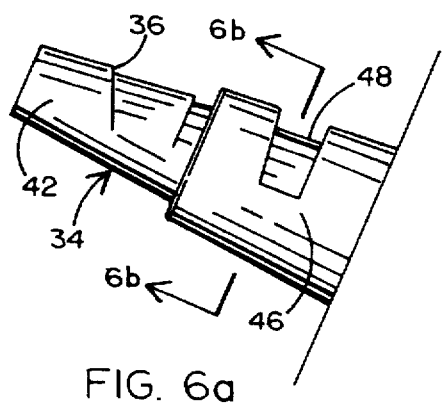
FIG. 6a is a side elevation and FIG. 6b an axial front elevation, of the connector of FIG. 5.
Figure 6B:
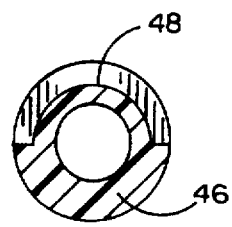

FIGS. 5 and 6 illustrate the application of the invention to a combo connector. The barbs 36 on the quarter-inch section 42 of the combo connector 34 are the same as on the connectors 30. On the 9.5 mm section 46 of connector 34, the barb takes the form of a half-circular recess 48 which, again, is present on only the upper half of the connector section 46.

FIG. 3 illustrates the fact that the barbs 36 merges gradually into the outer wall of connectors 30 and 32 at their circumferential extremeties to avoid any leak-prone axially extending ridges.

It is understood that the exemplary half-defined inlet connector for hardshell reservoirs described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

I claim:

1. A system for connecting a cardiotomy line to a hardshell reservoir, comprising:

a) a hardshell reservoir, said reservoir having a cover;

b) a substantially cylindrical connector disposed in proximity to said cover and extending substantially parallel thereto;

c) said connector having formed thereon an annular line attachment barb extending around only substantially one half of the circumference of said connector.

2. A connector for a cardiotomy line, comprising:

a) a substantially cylindrical connector having an outer diameter;

b) said connector having formed thereon an annular line attachment barb having an outer diameter and extending around only substantially one half of the circumference of said connector; and c) said connector axially having a first section of smaller diameter, and a second section of larger diameter, each of said sections having at least one barb, said barb extending around only substantially one half of the circumference of said connector.

3. A connector for a cardiotomy line, comprising:

a) a substantially cylindrical connector having an outer diameter;

b) said connector having formed thereon an annular line attachment barb having an outer diameter and extending around only substantially one half of the circumference of said connector.

4. The connector of claim 3, in which the outer diameter of said barb gradually merges into the outer diameter of said connector at the circumferential ends of said barb.

* * * * *